US005480970A

United States Patent [19]
Pollak et al.

[11] Patent Number: 5,480,970
[45] Date of Patent: Jan. 2, 1996

[54] METAL CHELATORS

[75] Inventors: Alfred Pollak; Anne Goodbody, both of Toronto, Canada

[73] Assignee: Resolution Pharmaceuticals, Mississauga, Canada

[21] Appl. No.: 171,737

[22] Filed: Dec. 22, 1993

[51] Int. Cl.$^6$ .............................. A61K 38/00; C07K 5/00; C07K 7/00
[52] U.S. Cl. .................... 530/328; 530/329; 530/330
[58] Field of Search .................... 530/30, 29, 28

[56] References Cited

U.S. PATENT DOCUMENTS

| | | | |
|---|---|---|---|
| 4,390,528 | 6/1983 | Najjar | 424/177 |
| 4,965,392 | 10/1990 | Fritzberg | 558/254 |
| 4,986,979 | 1/1991 | Morgan | 424/1.1 |
| 5,021,567 | 6/1991 | Johnson | 540/470 |
| 5,028,593 | 7/1991 | Nishioka | 514/18 |
| 5,071,965 | 12/1991 | Dunn | 534/14 |
| 5,082,930 | 1/1992 | Nicolotti | 530/402 |
| 5,091,514 | 2/1992 | Fritzberg | 534/14 |
| 5,112,594 | 5/1992 | Woulfe | 424/1.1 |

(List continued on next page.)

FOREIGN PATENT DOCUMENTS

| | | | |
|---|---|---|---|
| 352218 | 1/1990 | European Pat. Off. | C07D 471/08 |
| 569132 | 11/1993 | European Pat. Off. | C07F 13/00 |
| WO9103200 | 3/1991 | WIPO | |
| WO9213572 | 8/1992 | WIPO | A61K 49/02 |
| WO9219274 | 11/1992 | WIPO | A61K 49/02 |
| WO9219235 | 11/1992 | WIPO | A61K 31/15 |
| WO9310823 | 6/1993 | WIPO | A61K 49/02 |
| WO9315770 | 8/1993 | WIPO | A61K 49/02 |
| 9317719 | 9/1993 | WIPO | |
| WO9317719 | 9/1993 | WIPO | A61K 49/02 |
| WO9321962 | 11/1993 | WIPO | A61K 49/02 |
| WO9321957 | 11/1993 | WIPO | A61K 47/48 |

OTHER PUBLICATIONS

Nevrath, A. R., Kent, S. B. H., and Strick, N. (1984) J. Virol. Meth. 9, 341–346 "Monoclonal antibodies to hepatitis B surface . . .".
Babich et al J Nucl Med, 1993, 34:2176 "Tchnetium–99m–labeled chemotactic peptides:".
Clarke et al Coordination Chemistry Reviews, 1987, 78:253 "Medical diagnostic imaging with complexes of 99mTc".
Dewanjee et al Seminars in Nuclear Medicine vol XX, No. 1 (Jan.), 1990:5–27 "The chemistry of $^{99m}$Tc–labeled radiopharmaceuticals".
Fischman et al J Nucl Med, 1993, 23:2134 "In vivo bioactivity and biodistribution of chemotactic peptide analogs in nonhuman primates".
Fischman et al J Nuclear Med, 1991, 32(3):483 "Imaging focal sites of bacterial infection in rats with indium–111–labeled chemotactic peptide analogs".
Fridkin et al Mol Cell Biochem, 1981, 41:73 "Tuftsin, Thr–Lys–Pro–Arg".
McAfee et al Radiology, 1989, 171:593 "Update on radiopharmaceuticals for medical imaging".
Miller J nucl Med, 1993, 34(11):15N "Synthetic peptides come of age".
Olsen J Heterocycl Chem, 1970, 7(2):435 "Synthesis of quinoxaline peptides by the solid phase method".
Paik et al Int J Nucl Med Biol, 1985, 12(1):3 "The labeling of high affinity sites of antibodies with 99m–Tc".
Showell et al J Exp Med, 1976, 143:1154 "The structure–activity relations of synthetic peptides as chemotactic factors and inducers of lysosomal enzyme secretion for neutrophils".
Kaihara et al Chem Ab, 1961, 13678a "Quinaldylglycyltaurine: a urinary metabolite of quinaldic acid and kynurenic acid in the cat".

*Primary Examiner*—Jill Warden
*Assistant Examiner*—Benet Prickril
*Attorney, Agent, or Firm*—Foley & Lardner

[57] ABSTRACT

Radionuclide chelating compounds are provided for conjugation to targetting molecules such as proteins, peptides or antibodies. The resulting labelled targetting molecules may be used in diagnosis and therapy.

16 Claims, 2 Drawing Sheets

U.S. PATENT DOCUMENTS

| | | | |
|---|---|---|---|
| 5,112,595 | 5/1992 | Woulfe | 424/1.1 |
| 5,175,257 | 12/1992 | Kasina | 530/391.5 |
| 5,175,343 | 12/1992 | Fritzberg | 560/145 |
| 5,187,264 | 2/1993 | Verbruggen | 534/14 |
| 5,196,515 | 3/1993 | Lever | 530/363 |
| 5,202,109 | 4/1993 | Fritzberg | 424/1.1 |
| 5,202,451 | 4/1993 | Fritzberg | 556/419 |
| 5,220,000 | 6/1993 | Theodoropulos | 534/14 |
| 5,248,764 | 9/1993 | Flanagan | 530/324 |

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            formylated norleucine (formyl-Nleu)."

( i x ) FEATURE:
        ( A ) NAME/KEY: Modified-site
        ( B ) LOCATION: 4
        ( D ) OTHER INFORMATION: /note="X at position 4 is
            norleucine (Nleu)."

( x i ) SEQUENCE DESCRIPTION: SEQ ID NO:1:

Xaa  Leu  Phe  Xaa  Tyr  Lys  Lys  Asp  Xaa
    1                        5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Thr  Lys  Pro  Pro  Arg
    1                        5

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Lys   Pro   Pro   Arg
    1

( 2 ) INFORMATION FOR SEQ ID NO:4:

( i ) SEQUENCE CHARACTERISTICS:
            ( A ) LENGTH: 3 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note="Met is formylated."

( x i ) SEQUENCE DESCRIPTION: SEQ ID NO:4:

Met   Lys   Phe
    1

( 2 ) INFORMATION FOR SEQ ID NO:5:

( i ) SEQUENCE CHARACTERISTICS:
            ( A ) LENGTH: 6 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note="X at position 1 is
                    formylated norleucine (formyl-Nleu)."

( i x ) FEATURE:
            ( A ) NAME/KEY: Modified-site
            ( B ) LOCATION: 4
            ( D ) OTHER INFORMATION: /note="X at position 4 is
                    norleucine (Nleu)."

( x i ) SEQUENCE DESCRIPTION: SEQ ID NO:5:

Xaa   Leu   Phe   Xaa   Tyr   Lys
    1                       5

( 2 ) INFORMATION FOR SEQ ID NO:6:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /note="X at position 1 is
                    chelidamic acid (Chel)."

( i x ) FEATURE:
            ( A ) NAME/KEY: Modified-site
            ( B ) LOCATION: 3
            ( D ) OTHER INFORMATION: /note="Cys at position 3 is
                    substituted with acetamidomethyl (Acm)."

( x i ) SEQUENCE DESCRIPTION: SEQ ID NO:6:

Xaa   Gly   Cys   Gly
    1

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            dipicolinic acid (Dipic)."

( i x ) FEATURE:
        ( A ) NAME/KEY: Modified-site
        ( B ) LOCATION: 3
        ( D ) OTHER INFORMATION: /note="Cys at position 3 is
            substituted with acetamidomethyl (Acm)."

( x i ) SEQUENCE DESCRIPTION: SEQ ID NO:7:

Xaa  Gly  Cys  Gly
    1

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            picolinic acid (Pic)."

( i x ) FEATURE:
        ( A ) NAME/KEY: Modified-site
        ( B ) LOCATION: 3
        ( D ) OTHER INFORMATION: /note="Cys at position 3 is
            substituted with acetamidomethyl (Acm)."

( x i ) SEQUENCE DESCRIPTION: SEQ ID NO:8:

Xaa  Gly  Cys  Gly
    1

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            picolinic acid (Pic)."

( i x ) FEATURE:
        ( A ) NAME/KEY: Modified-site
        ( B ) LOCATION: 3
        ( D ) OTHER INFORMATION: /note="Cys at position 3 is
            substituted with acetamidomethyl (Acm)."

( x i ) SEQUENCE DESCRIPTION: SEQ ID NO:9:

Xaa  Ser  Cys  Gly  Thr  Lys  Pro  Pro  Arg 1          5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            picolinic acid (Pic)."

( i x ) FEATURE:
        ( A ) NAME/KEY: Modified-site
        ( B ) LOCATION: 3
        ( D ) OTHER INFORMATION: /note="Cys at position 3 is
            substituted with acetamidomethyl(Acm)."

( x i ) SEQUENCE DESCRIPTION: SEQ ID NO:10:

Xaa  Ser  Cys  Gly  Lys  Pro  Pro  Arg
1                        5

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            formylated norleucine (Nleu)."

( i x ) FEATURE:
        ( A ) NAME/KEY: Modified-site
        ( B ) LOCATION: 4
        ( D ) OTHER INFORMATION: /note="X at position 4 is
            norleucine (Nleu)."

( i x ) FEATURE:
        ( A ) NAME/KEY: Modified-site
        ( B ) LOCATION: 6
        ( D ) OTHER INFORMATION: /note="Lys at position 6 is
            substituted at the epsilon amino group with the
            peptide Pic- Gly-Cys-Gly- wherein Pic is picolinic
            acid."

( x i ) SEQUENCE DESCRIPTION: SEQ ID NO:11:

Xaa  Leu  Phe  Xaa  Tyr  Lys  Gly
1                   5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            formylated norleucine (Nleu)."

( i x ) FEATURE:
    ( A ) NAME/KEY: Modified-site
    ( B ) LOCATION: 4
    ( D ) OTHER INFORMATION: /note="X at position 4 is norleucin (Nleu)."

( i x ) FEATURE:
    ( A ) NAME/KEY: Modified-site
    ( B ) LOCATION: 6
    ( D ) OTHER INFORMATION: /note="Lys at position 6 is substituted at the epsilon amino group with the peptide Pic- Gly-Cys(Acm)-Gly- wherein Pic is picolinic acid."

( x i ) SEQUENCE DESCRIPTION: SEQ ID NO:12:

Xaa  Leu  Phe  Xaa  Tyr  Lys  Gly
1                   5

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is formylated norleucine (Nleu-for)."

( i x ) FEATURE:
        ( A ) NAME/KEY: Modified-site
        ( B ) LOCATION: 4
        ( D ) OTHER INFORMATION: /note="X at position 4 is norleucin (Nleu)."

( i x ) FEATURE:
        ( A ) NAME/KEY: Modified-site
        ( B ) LOCATION: 7
        ( D ) OTHER INFORMATION: /note="Lys at position 7 is substituted at the epsilon amino group with the peptide Pic- Gly-Cys(Acm)-Gly- wherein Pic is picolinic acid."

( x i ) SEQUENCE DESCRIPTION: SEQ ID NO:13:

Xaa  Leu  Phe  Xaa  Tyr  Lys  Lys  Asp  Gly
1                   5

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is formylated norleucine (Nleu-formyl)"

( i x ) FEATURE:
        ( A ) NAME/KEY: Modified-site
        ( B ) LOCATION: 4
        ( D ) OTHER INFORMATION: /note="X at position 4 is norleucine (Nleu)."

( x i ) SEQUENCE DESCRIPTION: SEQ ID NO:14:

```
    Xaa  Leu  Phe  Xaa  Tyr  Lys  Gly
    1                   5
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            formylated norleucine (Nleu-formyl)."

( i x ) FEATURE:
        ( A ) NAME/KEY: Modified-site
        ( B ) LOCATION: 4
        ( D ) OTHER INFORMATION: /note="X at position 4 is
            norleucine (Nleu)."

( x i ) SEQUENCE DESCRIPTION: SEQ ID NO:15:

```
    Xaa  Leu  Phe  Xaa  Tyr  Lys  Lys  Asp  Gly
    1                   5
```

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="X at position 1 is
            formylated norleucine (Nleu-formyl)."

( i x ) FEATURE:
        ( A ) NAME/KEY: Modified-site
        ( B ) LOCATION: 4
        ( D ) OTHER INFORMATION: /note="X at position 4 is
            norleucine (Nleu)."

( i x ) FEATURE:
        ( A ) NAME/KEY: Modified-site
        ( B ) LOCATION: 6
        ( D ) OTHER INFORMATION: /note="Lys at position 6 is
            substituted at the epsilon amino group with Gly."

( x i ) SEQUENCE DESCRIPTION: SEQ ID NO:16:

```
    Xaa  Leu  Phe  Xaa  Tyr  Lys  Gly
    1                   5
```

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
    Gly  Lys  Pro  Pro  Arg
    1                   5
```

( 2 ) INFORMATION FOR SEQ ID NO:18:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:18:

Gly Thr Lys Pro Pro Arg
1               5

( 2 ) INFORMATION FOR SEQ ID NO:19:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="X at position 1 is
formylated norleucine (Nleu-formyl)."

( i x ) FEATURE:
( A ) NAME/KEY: Modified-site
( B ) LOCATION: 4
( D ) OTHER INFORMATION: /note="X at position 4 is
norleucine (Nleu)."

( i x ) FEATURE:
( A ) NAME/KEY: Modified-site
( B ) LOCATION: 7
( D ) OTHER INFORMATION: /note="Lys at position 7 is
substituted at the epsilon amino group with Gly."

( x i ) SEQUENCE DESCRIPTION: SEQ ID NO:19:

Xaa Leu Phe Xaa Tyr Lys Lys Asp Gly
1               5

METAL CHELATORS

FIELD OF THE INVENTION

This invention is in the field of diagnostic imaging, and relates to chemical chelators useful in the radiolabelling of agents that target tissues of diagnostic and therapeutic interest.

BACKGROUND OF THE INVENTION

The art of diagnostic imaging exploits contrasting agents that in binding or localizing site selectively within the body, help to resolve the image of diagnostic interest. $^{67}$Gallium salts, for example, have an affinity for tumours and inflamed tissue and, with the aid of scanning tomography, can reveal afflicted body regions to the physician. Other contrasting agents include the metal radionuclides such as $^{99m}$technetium and $^{186/188}$rhenium, and these have been used to label targetting molecules, such as proteins, peptides and antibodies that localize at desired regions of the human body.

As targetting agents, proteins and other macromolecules can offer the tissue specificity required for diagnostic accuracy; yet labelling of these agents with metal radionuclides is made difficult by their physical structure. Particularly, protein and peptide targetting agents present numerous sites at which radionuclide binding can occur, resulting in a product that is labelled heterogeneously. Also, despite their large size, proteins rarely present the structural configuration most appropriate for high affinity radionuclide binding, i.e. a region incorporating four or more donor atoms that form five-membered rings. As a result, radionuclides are bound typically at the more abundant low-affinity sites, forming unstable complexes.

To deal with the problem of background binding, Paik et al (Nucl Med Biol 1985, 12:3) proposed a method whereby labelling of antibody is performed in the presence of excess DPTA (diaminetrimethylenepentaacetic acid), to mask the low affinity binding sites. While the problem of low affinity binding is alleviated by this method, actual binding of the radionuclide, in this case technetium, was consequently also very low. The direct labelling of proteins having a high proportion of cysteine residues also has been demonstrated (Dean et al; WO 92/13,572). This approach exploits thiol groups of cysteine residues as high-affinity sites for radionuclide binding, and is necessarily limited in application to those targetting agents having the required thiol structure.

A promising alternative to the direct labelling of targetting agents is an indirect approach, in which targetting agent and radionuclide are conjugated using a chelating agent. Candidates for use as chelators are those compounds that bind tightly to the chosen metal radionuclide and also have a reactive functional group for conjugation with the targetting molecule. For use in labelling peptide and protein-based targetting agents, the chelator is ideally itself peptide-based, to allow the chelator/targetting agent to be synthesized in any desired structural combination using peptide synthesis techniques. For utility in diagnostic imaging, the chelator desirably has characteristics appropriate for its in vivo use, such as blood and renal clearance and extravascular diffusibility.

SUMMARY OF THE INVENTION

The present invention provides chelators that bind diagnostically useful metals, and can be conjugated to targetting agents capable of localizing at body sites of diagnostic and therapeutic interest. The chelators of the present invention are peptide analogues designed structurally to present an N$_3$S configuration capable of binding oxo, dioxo and nitrido ions of radionuclides such as $^{99m}$technetium and $^{186/188}$rhenium.

More particularly, and according to one aspect of the invention, there are provided metal chelators of the formula:

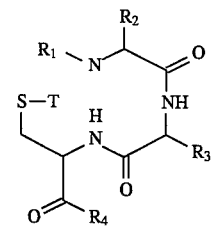

wherein

R$_1$ and R$_2$ together form a 5- or 6-membered heterocyclic ring which is optionally fused to a 5- or 6-membered ring, wherein either ring is optionally substituted with a conjugating group or with a conjugating group having a targetting molecule coupled thereto or a hydroxyl group;

R$_3$ is selected from H; alkyl; and alkyl substituted by a group selected from amino, aminoacyl, carboxyl, guanidinyl, hydroxyl, thiol, phenyl, phenolyl, indolyl and imidazolyl;

R$_4$ is selected-from hydroxyl; alkoxy; any amino acid residue; and a targetting molecule; and T is H or a sulfur protecting group;

In an aspect of the invention, chelators of the above formula are provided in a form having a diagnostically or therapeutically useful metal complexed therewith.

According to another aspect of the invention, the chelator is provided in a form coupled to a diagnostically or therapeutically useful targetting molecule. An additional aspect of the invention provides the chelators coupled to a targetting molecule and in a form having a metal complexed therewith.

In another aspect of the invention, targetting molecules are provided having the general sequence: (SEQ. ID NO: 1) formyl-Nleu-Leu-Phe-Nleu-Tyr-Lys-Lys-Asp-X-OH wherein X is a bond or an amino acid residue; the targetting molecule which may be coupled to chelators of the present invention.

DETAILED DESCRIPTION OF THE FIGURES

Figure 1:
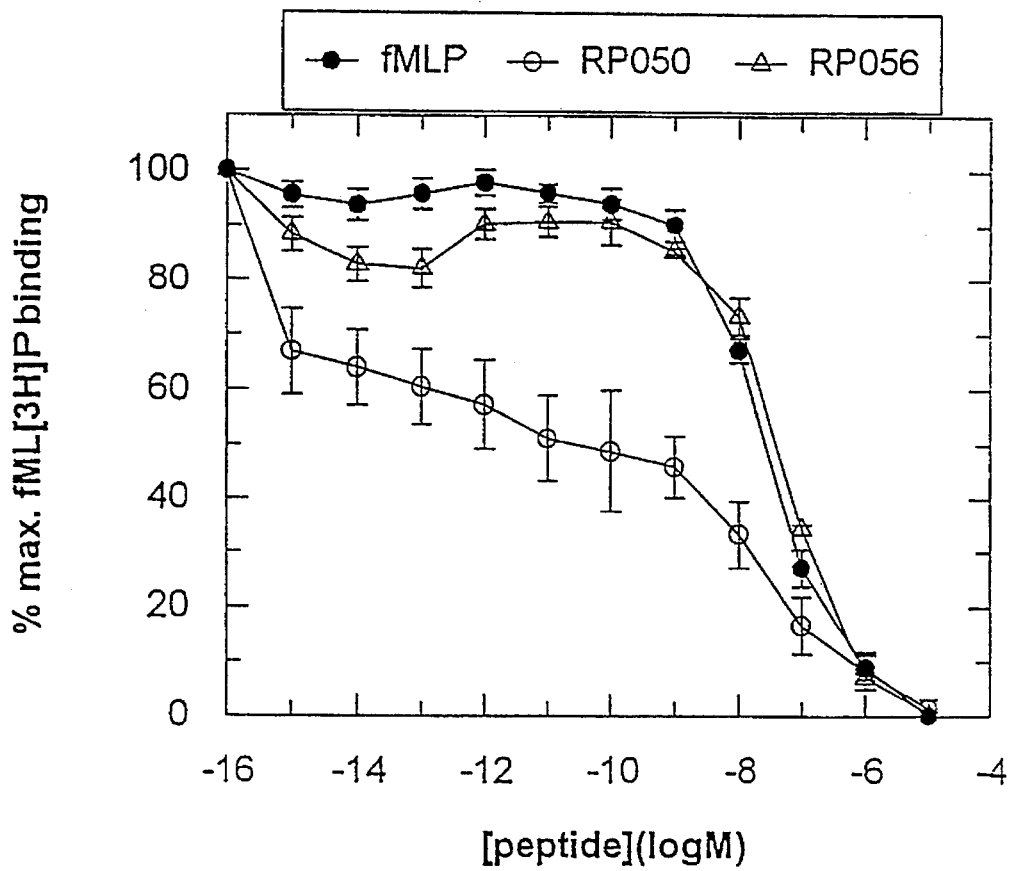
FIG. 1 is a graph representing binding affinity of targetting molecules in accordance with an embodiment of the invention.

The invention provides chelators of diagnostically useful metals that when complexed with the metal and in a form conjugated to a targetting molecule are useful for delivering the detectable metal to a body site of diagnostic interest. As illustrated in the above formula, the chelators are peptidic derivatives that present an N$_3$S configuration in which the metal is complexed.

Terms defining the variables R$_1$–R$_4$ and T as used hereinabove have the following meanings:

"alkyl" refers to a straight or branched $C_1$–$C_8$ chain and includes lower $C_1$–$C_4$ alkyl;

"alkoxy" refers to straight or branched $C_1$–$C_8$ alkoxy and includes lower $C_1$–$C_4$ alkoxy;

"thiol" refers to a sulfhydryl group that may be substituted with an alkyl group to form a thioether;

"sulfur protecting group" refers to a chemical group that inhibits oxidation of sulfur and includes groups that are cleaved upon chelation of the metal. Suitable sulfur protecting groups include known alkyl, aryl, acyl, alkanoyl, aryloyl, mercaptoacyl and organothio groups.

In preferred embodiments of the invention, the chelators conform to the above formula in which: $R_1$ and $R_2$ together form a six member heterocyclic ring; $R_3$ is selected from H and a hydroxyl substituted alkyl group selected from methyl and ethyl and most preferably hydroxymethyl; $R_4$ is selected from hydroxyl; alkoxy; an amino acid residue; and a targetting molecule; and T is a hydrogen atom or the sulfur protecting group acetamidomethyl (Acm);

In specific embodiments of the invention, the chelators conform to the above general formula wherein T is the sulfur protecting group acetamidomethyl (Acm); $R_3$ is H or hydroxymethyl; $R_1$ and $R_2$ together form a pyridine ring and $R_4$ is a glycine amino acid residue or a glycine residue attached to a targetting peptide.

The substituents represented by $R_1$ and $R_2$ together with the adjacent nitrogen atom form a 5- or 6-membered heterocyclic ring which may be fused to another five or six membered ring. Five and six membered heterocyclic rings include but are not limited to pyrole, pyrazole, imidazole, pyridine, pyrazine, pyridazine, pyrimidine and triazine. Fused rings include but are not limited to N-containing bicyclics such as quinoline, isoquinoline, indole and purine. Rings containing sulfur atoms e.g. thiazole and oxygen atoms e.g. oxazole are also encompassed by the present invention.

The heterocyclic ring formed by $R_1$ and $R_2$ may be substituted with a conjugating group that is chemically reactive allowing for coupling a targetting molecule to the chelator. In the preferred case where the targetting molecule is peptidic, the conjugating group is reactive under conditions that do not denature or otherwise adversely affect the peptide. In one embodiment of the invention, the conjugating group is reactive with a functional group of the peptide/protein such as the carboxy terminus or amino terminus. Alternatively, the conjugating group can be reactive with an ε-amino group of a lysine residue. Conjugating groups reactive with amino groups of targetting molecules include carboxyl and activated esters. Conjugating groups reactive with carboxyl groups of targetting molecules include amines and hydrazines.

For diagnostic and therapeutic purposes, the chelator per se may be used in combination with a detectable; metal capable of forming a complex. Suitable metals include radionuclides such as technetium and rhenium in their various forms such as $^{99m}TcO^{3+}$, $^{99m}TcO_2^+$, $ReO^{3+}$ and $ReO_2^+$. More desirably, the chelator is coupled to a targetting molecule that serves to localize the chelated metal to a desired location for diagnostic imaging or for therapy i.e. radiation therapy of tumours. Examples of targetting molecules include, but are not limited to, steroids, proteins, peptides, antibodies, nucleotides and saccharides. Preferred targetting molecules include proteins and peptides, particularly those capable of binding with specificity to cell surface receptors characteristic of a particular pathology. For instance, disease states associated with over-expression of particular protein receptors can be imaged by labelling that protein or a receptor binding fragment thereof in accordance with the present invention. Peptide-based targetting molecules can be made, either per se or as chelator conjugates, by various known methods or in some instances can be commercially obtained. Solid phase synthesis employing alternating t-Boc protection and deprotection is the preferred method of making short peptides which can be an automated process. Recombinant DNA technology is preferred for producing proteins and long fragments thereof.

Chelators of the present invention are peptide derivatives and are most efficiently prepared by solid-phase peptide synthesis. In general solid-phase synthesis involves the stepwise addition of amino acid residues to a growing peptide chain that is linked to an insoluble support or matrix, such as polystyrene. The C-terminus residue of the chelator is first anchored to a commercially available support with its amino group protected with an N-protecting agent such as a t-butyloxycarbonyl group (tBoc) or a fluorenylmethoxycarbonyl (FMOC) group. The amino protecting group is removed with suitable deprotecting agents such as TFA in the case of tBOC or piperadine for FMOC and the next amino acid residue (in N-protected form) is added with a coupling agent such as dicyclocarbodiimide (DCC). Upon formation of a peptide bond the reagents are washed from the support. After addition of the final residue, the chelator is cleaved from the support with a suitable reagent such as trifluoroacetic acid (TFA) or hydrogen fluoride (HF) and isolated.

The present invention encompasses chelators incorporating various heterocyclic groups containing a nitrogen atom provided that it is analogous in structure to an amino acid in that there is a carboxyl carbon, alpha carbon and an alpha nitrogen wherein the alpha carbon and alpha nitrogen are incorporated in a common ring. For example, picolinic acid (pic), dipicolinic acid (dipic), chelidamic acid (chel), 2-carboxypyrazine, 2-carboxypyrimidine and the like will behave as a natural amino acid residue in solid phase synthesis by forming a peptidic bond upon reaction of the carboxyl group and a deprotected amino group of a previously added residue. Other possible rings include but are not limited to five membered rings such as 2-carboxyimidazole, bicyclics such as 2-carboxyquinoline as well as rings containing additional nitrogen atoms or sulfur or oxygen atoms. Variation at $R_3$ may be introduced by incorporation of various amino acid residues at the appropriate stage of chain elongation. For example, $R_3$ may be a hydroxymethyl group simply by using a serine residue or may be a hydrogen atom by using glycine. Any D or L, naturally occurring or derivatized amino acid may be used.

In accordance with an embodiment of the present invention, $R_4$ is a targetting molecule that is proteinaceous. Human Immunoglobulin G (HIG), a multisubunit protein, has been directly labelled with technetium-99m and used extensively for imaging sites of inflammation, however smaller peptides are becoming the targetting molecules of choice for their site specificity as a result of receptor binding properties and for their ease of preparation. An example of a peptidic targetting molecules are Tuftsin antagonists such as (SEQ. ID NO: 2) Thr-Lys-Pro-Pro-Ar and (SEQ. ID NO: 3) Lys-Pro-Pro-Arg. Another peptidic targetting molecule useful for imaging inflammation is fMLP (SEQ. ID NO: 4) (formyl-Met-Lys-Phe) and derivatives thereof such as (SEQ. ID NO: 5) formyl-Nleu-Leu-Phe-Nleu-Tyr-Lys described by Fischman et al in pending Canadian application CA 2,016, 235. It is believed that fMLP and various derivatives thereof bind to neutrophils and are therefore useful in imaging sites of inflammation.

In accordance with another aspect of the invention, the present invention provides a peptide useful as a targetting molecule which has the sequence (SEQ. ID NO: 1) formyl-Nleu-Leu-Phe-Nleu-Tyr-Lys-Lys-Asp-X-OH wherein X is a bond or any aminoacid residue. For convenient synthesis of this peptide, X is preferrably a glycine (Gly) residue. In vivo studies have shown this peptide coupled to a chelator of the present invention strongly binds to neutrophils while having a more favourable neutropenic profile than native fMLP or the derivative (SEQ. ID NO: 5) formyl-Nleu-Leu-Phe-Nleu-Tyr-Lys.

Synthesis of the chelator/targetting molecule conjugate can be achieved in various ways. When $R_4$ is a peptidic targetting molecule, it is convenient to synthesize the chelator/targetting molecule conjugate in toto by starting solid-phase synthesis from the C-terminus residue of the targetting molecule and ending with the heterocyclic residue ($R_1$, $R_2$) of the chelator. When a targetting molecule incorporates a lysine residue it may be coupled to the chelator at $R_4$ by way the ε-amino group of the lysine residue. In this case, the targetting peptide is synthesized as a separate chain from the chelator and is differentially protected at the ε-amino group and N-terminus amino group. For example the ε-amino group may be protected with 1-(4,4-dimethyl-2,6-dioxocyclohexylidine)-ethyl (Dde) while the N-terminus amino is FMOC protected. When the targetting molecule synthesis is complete the ε-amino group is deprotected with hydrazine and is available for reaction with a C-terminus carboxyl group of a chelator while the N-terminus amino group is protected.

Alternatively, targetting molecules may also be conjugated to the chelator by way of a conjugating group substituent on the heterocyclic ring of the chelator. For example, a chelator with an amino substituent on the heterocyclic ring upon deprotection will be reactive with the C-terminus carboxyl group of a peptide targetting molecule. Such a conjugate may be synthesized as a single chain starting at the C-terminus residue of the chelator and ending with the N-terminus of the targetting molecule. Alternatively, a peptide targetting molecule may be conjugated to the heterocyclic residue by way of its N-terminus when the heterocyclic group has a suitable conjugating group substituent such as a carboxyl group or an activated ester. In this case, the chelator and targetting molecule are synthesized as separate chains and then coupled to form the desired conjugate.

In accordance with one aspect of the invention, chelators incorporate a diagnostically or therapeutically useful metal. Incorporation of the metal within the chelator can be achieved by various methods common to the art of coordination chemistry. When the metal is the radionuclide technetium-99m, the following general procedure may be used to form a technetium complex. A chelator solution is formed initially by dissolving the chelator in aqueous alcohol eg. ethanol-water 1:1. The solution is degassed with nitrogen to remove oxygen then the thiol protecting group is removed, for example with sodium hydroxide and heat. The solution is then neutralized with an organic acid such as acetic acid (pH 6.0–6.5). In the labelling step, sodium pertechnetate is added to the chelator solution with an amount of stannous chloride sufficient to reduce the technetium. Sodium pertechnetate is obtained from a Molybdenum generator. The solution is mixed and left to react at room temperature and then heated on a water bath. In an alternative method, labelling can be accomplished as with the chelator solution adjusted to pH 8. Pertechnetate may be replaced with a solution of technetium complexed with labile ligands suitable for ligand exchange reactions with the desired chelator.

Suitable ligands include tartarate, citrate and glucoheptonate. Stannous chloride may be replaced with sodium dithionite as the reducing agent if the chelating solution is alternatively adjusted to pH 12–13 for the labelling step. The labelled chelator may be separated from contaminants $^{99m}TcO_4^-$ and colloidal $^{99m}TcO_2$ chromatographically, e.g. with a C-18 Sep Pak cartridge activated with ethanol followed by dilute HCl. Eluting with dilute HCl separates the $^{99m}TcO_4^-$, and eluting with EtOH-saline 1:1 brings off the chelator while colloidal $^{99m}TcO_2$ remains on the column. The chelators of the invention can be coupled to a targetting molecule prior to labelling with the radionuclide, a process referred to as the "bifunctional chelate" method. An alternative approach known as the "prelabelled ligand" method, the chelator is first labelled with the desired metal and is subsequently coupled to the targetting molecule. This method is advantageous in that the targetting molecule itself is not inadvertently labelled at low affinity binding sites which may render the targetting molecule inactive or undesirably release the metal in vivo.

An alternative approach for labelling chelators of the present invention involves techniques described in a copending U.S. application by Pollak et al, filed on 16 Nov. 1993, incorporated herein by reference. Briefly, chelators are immobilized on a solid phase support in such a manner that they are released from the support only upon formation of a complex with the labelling metal atom. This is achieved when the chelator is coupled to a functional group of the support by one of the complexing atoms. Preferably, a complexing sulfur atom is coupled to the support which is functionalized with sulfur a protecting group such as maleimide.

When coupled to a targetting molecule and labelled with a diagnostically useful metal, chelators of the present invention can be used to detect pathological conditions by techniques common in the art. A chelator/targetting molecule conjugate labelled with a radionuclide metal such as technetium may be administered to a mammal by intravenous injection in a pharmaceutically acceptable solution such as saline or DMSO. The amount of labelled conjugate administered is dependent upon the toxicity profile of the chosen targetting molecule as well as the metal. Localization of the metal in vivo is tracked by standard scintigraphic techniques at appropriate time intervals subsequent to administration.

The following examples are presented to illustrate certain embodiments of the present invention.

EXAMPLE 1 Preparation of Chelators and Targetting molecules

Chelators were synthesized using 9-fluorenylmethyloxycarbonyl (FMOC) chemistry on an 2-methoxy-4-alkoxybenzyl alcohol resin preloaded with the protected C-terminus residue (Sasrin resin, Bachem Biosciences Inc., Philadelphia Pa.) using an Applied Biosystems 433A peptide synthesizer (Foster City, Calif.). N-terminus residues Pic, DiPic and Chel were incorporated by using picolinic, dipicolinic and chelidamic acid respectively as the final residue in the synthesis.

Preparation of Chelators (SEQ. ID NO: 6) RP-043 Chel-Gly-Cys(Acm)-Gly-OH (SEQ. ID NO: 7) RP-044 DiPic-Gly-Cys (Acm)-Gly-OH (SEQ. ID NO: 8) RP-049 Pic-Gly-Cys(Acm)-Gly-OH The chelator-resin was dried in vacuo for 12 hours. Cleavage of the chelator from the resin involved mixing a cooled solution of 95% trifluoroacetic acid (TFA) and 5% water (1 ml per 100 mg of peptide-resin) with the peptide-resin for 1.5 to 2 hours at room temperature. The resin was removed by filtration and washed 3 times with 30 ml t-butyl methyl ether in a 50 ml conical polypropylene centrifuge tube forming a white precipitate. The precipitate was dissolved in water with added acetonitrile. The precipitate was frozen in acetone-dry ice and lyophilized over 12 hours. The resulting white powder was dissolved in water, filtered through a 0.45 µm syringe filter (Gelman Acrodisc LC PVDF) and purified by reversed-phase HPLC (Beckman System Gold) with a C18 column .(Waters RCM 25×10) using 0.1% TFA in water as buffer A and 0.1% TFA in acetonitrile as buffer B. The column was equilibrated with 100:0 buffer A:buffer B and eluted with a linear gradient in 25 min at 1 ml/min to 50% buffer B. Fractions were reanalysed on the HPLC and pooled according to matching profiles. If necessary the pooled fractions were repurified using the same conditions. The pure fractions were frozen in acetone-dry ice and lyophilized over 10 hours to give a white powder.

Preparation of Chelator-Targetting Agent Conjugates (SEQ. ID NO: 9) RP-063 (Pic-Ser-Cys(Acm)-Gly)-Thr-Lys-Pro-Pro-Arg-OH (SEQ. ID NO: 10) RP-065 (Pic-Ser-Cys(Acm)-Gly)-Lys-Pro-Pro-Arg-OH Synthesis began from the Arg residue preloaded on the resin and continued to the Ser residue of the chelator ending with the addition of picolinic acid. The chelator-peptide-resin was dried in vacuo 12 hours. Cleavage from the resin involved mixing with a solution of 10 ml trifluoroacetic acid (TFA), 0.5 ml water, 0.5 ml thioanisole, 0.25 ml 1,2-ethanedithiol (EDT) and 0.75 g phenol for 1.5 to 2 hours at room temperature. The resin was removed by filtration and the peptide washed 3 times with 30 ml t-butyl methyl ether in a 50 ml conical polypropylene centrifuge tube forming a white precipitate. The precipitate was dissolved in water with added acetonitrile when solubility problems arose. The precipitate was frozen in acetone-dry ice and lyophilized over 12 hours. The resulting white powder was dissolved in water, filtered through a 0.45 µm syringe filter (Gelman Acrodisc LC PVDF) and purified by reversed-phase HPLC (Beckman System Gold) with a C18 column (Waters RCM 25×10) using 0.1% TFA in water as buffer A and 0.1% TFA in acetonitrile as buffer B. The column was equilibrated with 100:0 buffer A:buffer B and eluted with a linear gradient in 25 min at 1 ml/min to 50% buffer B. Fractions were reanalysed on the HPLC and pooled according to matching profiles. If necessary the pooled fractions were repurified using the same conditions. The pure fractions were frozen in acetone-dry ice and lyophilized over 10 hours to give a white powder.

Preparation of Chelator-fMLP Peptide Conjugates (SEQ. ID NO: 11) RP-022 (Pic-Gly-Cys-Gly)-εNH-Lys(-Gly-OH)-Tyr-Nleu-Phe-Leu-Nleu-for (SEQ. ID NO: 12) RP-050 (Pic-Gly-Cys(Acm)-Gly)-εNH-Lys(-Gly-OH)-Tyr-Nleu-Phe-Leu-Nleu-for (SEQ. ID No. 13) RP-056 (Pic-Gly-Cys(Acm)-Gly)-ε-NH-Lys(-Asp-Gly-OH)-Lys-Tyr-Nleu-Phe-Leu-Nleu-for Targetting peptides that comprise lysine residues can be coupled to the chelator via the Lys ε-amino group by the following procedure. For RP-022, RP-050 and RP-056 the targetting peptide was initially synthesized from glycine to norleucine by 9-fluorenylmethyloxycarbonyl (FMOC) chemistry using an FMOC-glycine preloaded 2-methoxyl-4-alkoxyl-benzyl alcohol resin and a 1-(4,4-dimethyl-2,6-dioxocyclohexylidine)-ethyl (Dde) orthogonal protected lysine with an Applied Biosystems 433A peptide synthesizer. The fMLP peptide-resin was removed from the synthesizer and dried 12 hours in vacuo to prepare for formylation.

Formic anhydride was prepared by heating acetic anhydride (2 equivalents) with formic acid (1 equivalent) to 50° C. for 15 minutes followed by cooling to 0° C. Formylation of the fMLP peptide involved swelling the peptide-resin in dichloromethane (DCM) (5 ml) followed by swirling with formic anhydride (5 ml) for 15 minutes. The formylated fMLP peptide-resin was filtered, washed with DCM and dried in vacuo 12 hours.

Formylated peptide-resin (50 mg/2 ml) was swirled with a 2% hydrazine hydrate in N-methylpyrrolidone (NMP) solution for 3 minutes two times then filtered and washed with DCM and dried in vacuo 12 hours to remove the ε-amino lysine protecting group (Dde) while leaving the N-terminus amino group formylated.

The chelator was added to the ε-amino lysine of the fMLP peptide on the 433A peptide synthesizer. The chelator-peptide-resin was dried in vacuo 12 hours. Cleavage from the resin involved mixing a cooled solution of 95% trifluoroacetic acid (TFA) and 5% water (1 ml per 100 mg of chelator-peptide-resin) with the chelator-peptide-resin for 1.5 to 2 hours at room temperature. The resin was removed by filtration and washed with 1–3 ml of TFA to obtain 6–8 ml of a clear yellow liquid. This liquid was slowly dropped into 30–35 ml of tert-butyl methyl ether in a 50 ml conical polypropylene centrifuge tube forming a white precipitate. The precipitate was centrifuged at 7000 rpm, 0° C. for 5 minutes (Sorvall RT 6000, Dupont), decanted and washed two more times with t-butyl methyl ether. Following drying under vacuum the precipitate was dissolved in water with added acetonitrile when solubility problems arose. The precipitate was frozen in acetone-dry ice and lyophilized over 10 hours. The resulting white powder was dissoved in dimethylsulfoxide (20 µL) and 50:50 acetonitrile:water solution (980 µL), filtered through a 0.45 µm syringe filter (Gelman Acrodisc LC PVDF), and purified by reversed-phase HPLC (Beckman System Gold) with a C18 column (Waters RCM 25×10) using 0.1% TFA in water as buffer A and 0.1% TFA in acetonitrile as buffer B. The column was equilibrated with 50:50 buffer A:buffer B and eluted with a linear gradient in 25 min at 1 ml/min to 100% buffer B. Fractions were reanalysed on the HPLC and pooled according to matching profiles. If necessary, the pooled fractions were repurified using the same conditions. The pure fractions were frozen in acetone-dry ice and lyophilized over 12 hours to give a white powder.

EXAMPLE 2 Labelling Chelators with $^{99m}Tc$

Chelators (1 mg) were dissolved in 200 µL EtOH-water (1:1) in a tube. 100–200 µL sodium pertechnetate (200–600 MBa, 5–15 mCi), 100 µL phosphate buffer (0.25M, pH 7.4), and 200 µL of a solution containing 50 µg stannous chloride dihydrate and 40 mg sodium tartrate were added to the tube and capped tightly and placed in a boiling water bath for 10 minutes. In order to achieve adequate separation of the chelators, the solution was then loaded on a C-18 Sep-Pak column activated by washing sequentially with 5 ml methanol, 10 ml water and 5 ml dilute (1 mM) HCl to remove $TcO_4^-$. Subsequent elution with 2 ml EtOH-saline (1:1) removed the chelator while $TcO_2$ remained on the column. The extent of complexation of $^{99m}Tc$ with chelators was measured by radioactivity of the eluted fractions.

| Chelator (EtOH-saline eluate) | |
| --- | --- |
| RP-022 | 29 |
| RP-043 | 7 |
| RP-049 | 92 |
| RP-050 | 63 |
| RP-056 | 78 |
| RP-063 | 93 |
| RP-065 | 92 |

*units of measure in MBq with corresponding percent of total

EXAMPLE 3 In vivo Imaging and Biodistribution of Chelators

Rat inflammation studies were performed as follows. 2 male Wistar rats (Charles River, 150–200 g) were injected intramuscularly with zymosan, a yeast cell wall preparation (5 mg) or virulent *E. coli* (ATCC 25922, 0.1 ml of $0.5\times10^9$ organisms/ml) suspension into their left hindlegs 24 hours before imaging. Focal inflammation in the leg was visually detectable after 1 day. 1 mg (ca. 0.7 μMol) of the chelator was dissolved in 50 μL of dimethylsulfoxide and added to an ethanol-water mixture (1:1, 200 μL). An aliquot of Tc-99m tartarate (ca. 400 MBq) was added and transchelation allowed to proceed for 20 min. at 100° C. The Tc-99m chelate was purified by elution through a Sep Pak cartridge. The purified tracer solution was further diluted with saline to prepare an injectable (200 μL) containing about 100 μCi (3.7 MBq) of activity.

The rats were anaesthetized with somnitol (40 to 50 mg/kg), and the Tc-99m chelate solution (200 μL) was injected intravenously via the tail vein. Serial whole-body scintigrams were acquired for the first 5 minutes. Subsequently, further images were obtained at 30, 60, and 120 minutes. The rats were then killed with anaesthesia and samples of organs, urine, blood, inflamed muscle (left leg) and non-inflamed muscle (right leg) were weighted and counted in either a well-type gamma counter or in a gamma dose calibrator. The dose calculations were made based on assumption that the rat weighed 200 g and that the blood volume constituted 8% of body weight. Results are averages for two rats and are corrected for the residual dose in the tail.

EXAMPLE 4 Neutrophil Binding Assay of fMLP and Chelator-fMLP Derivative Conjugates RP-050 and RP-056

Rat peripheral neutrophils were prepared for binding assay as follows: blood was obtained by cardiac puncture and anticoagulated with acid-citrate dextrose (ACD) (10%). Red blood cells were removed by sedimentation on hydroxyethyl cellulose (1.1%) for 30 min at room temperature and leukocyte-rich supernatant layered onto 65% percol. Centrifugation at 400 g for 30 min resulted in a distinct band of mononuclear cells (lymphocytes and monocytes) which was discarded, the neutrophil rich pellet was resuspended and remaining red blood cells lysed by hypotonic shock using cold water. The remaining neutrophils were resuspended in Hanks Buffered Salt Solution (HBSS) to the desired concentration. Final neutrophil preparation consisted of cells pooled from up to 10 animals, > 90% neutrophils and > 95% viable by Trypan Blue exclusion.

Binding affinity of the test peptides was assessed by competing off a constant concentration of tritiated fMLP of known affinity for neutrophil receptors. $10^6$ neutrophils were added to polypropylene plates containing 15 nM tritiated fMLP and varying concentrations of unlabelled test peptides in a final volume of 150 μL HBSS. The plate was incubated for 1 hour at room temperature after which cells were harvested by filtration onto glass fibre filter mats (Skatron receptor binding filtermat) using a Skatron cell harvester with 12 well head. Harvested cells were washed with ice-cold saline and air dried. Filters were then placed in 6 ml scintillation vials, 5 ml of scintillation fluid added (Ecolume) and vials counted using a liquid scintillation counter. Binding affinity of the test peptides is illustrated in FIG. 1 and expressed as % maximal tritiated fMLP binding vs. peptide concentration. % maximal tritiated fMLP binding= (specific binding÷ maximum binding)×100%. Specific binding was the total binding less non-specific binding which was the amount of residual radioactivity bound in the presence of 10 μM unlabelled fMLP. Both RP-050 and RP-056 had greater binding affinity for neutrophil receptors than native fMLP.

| | In vivo Distribution | | | | | | | | | |
| --- | --- | --- | --- | --- | --- | --- | --- | --- | --- | --- |
| | blood | liver | kidney | urine | GI tract | time (min) | Inflam muscle | Uninfl muscle | Inflam agent | Infl: Uninfl | time (min) |
| | | | (% per organ) | | | | | (% per gm) | | | |
| RP-022 | 3.036 | 35.26 | 18.82 | 8.400 | 41.285 | 90 | | | | | |
| RP-043 | 1.016 | 0.953 | 4.359 | 33.950 | 52.619 | 88 | | | | | |
| RP-049 | 0.187 | | 21.700 | | | | 0.077 | 0.019 | E. coli | 4.24 | |
| RP-050 | 3.436 | 20.866 | 11.470 | 14.050 | 25.777 | 109 | | | E. coli | 3.17 | |
| RP-063 | 6.370 | 3.050 | 4.170 | 44.710 | 5.080 | 30 | 0.180 | 0.050 | E. coli | 3.62 | 30 |
| RP-065 | 3.520 | | | 53.000 | | 30 | 0.125 | 0.059 | E. coli | 2.1 | |
| RP-056 | | | | | | | 0.143 | 0.041 | E. coli | 3.52 | 45 |
| IgG | 48 | | | | | 120 | 0.104 | 0.052 | E. coli | 2.07 | 120 |

EXAMPLE 5 Neutropenia Assay of fMLP, fMLP derivative formyl-Nleu-Leu-Phe-Nleu-Tyr-Lys (SEQ. ID NO: 5) and (SEQ. ID NO: 13) RP-056 (Pic-Gly-Cys(Acm)-Gly-ε-NH-Lys(A-Asp-Gly-OH)-Lys-Tyr-Nleu-Phe-Leu-Nleu-for The effect of fMLP, fMLP derivative formyl-Nleu-Phe-Nleu-Tyr-Lys and Chelator-peptide conjugate RP-056 on circulating neutrophil number was assessed using the rat transient neutropenia model. Rats were anaesthetized with 250 μL somnitol (16 mg/rat) and injected via the tail vein at T= 0 with the test peptides. At a range of time points after injection (0, 2, 5, 10, 30 min) a 2 ml blood sample was taken by cardiac puncture (anticoagulated with 10% ACD). 3 animal were used per time point. For each sample the total white blood cells/ml and % neutrophils was determined, the number of neutrophils/ml in each sample being calculated.

Within each experiment the number neutrophils/ml after saline injection at all time points was meaned to give a saline control against which the peptides could be compared. The number neutrophils/ml after peptide injection was expressed as a % of the saline control within each experiment.

Figure 2:
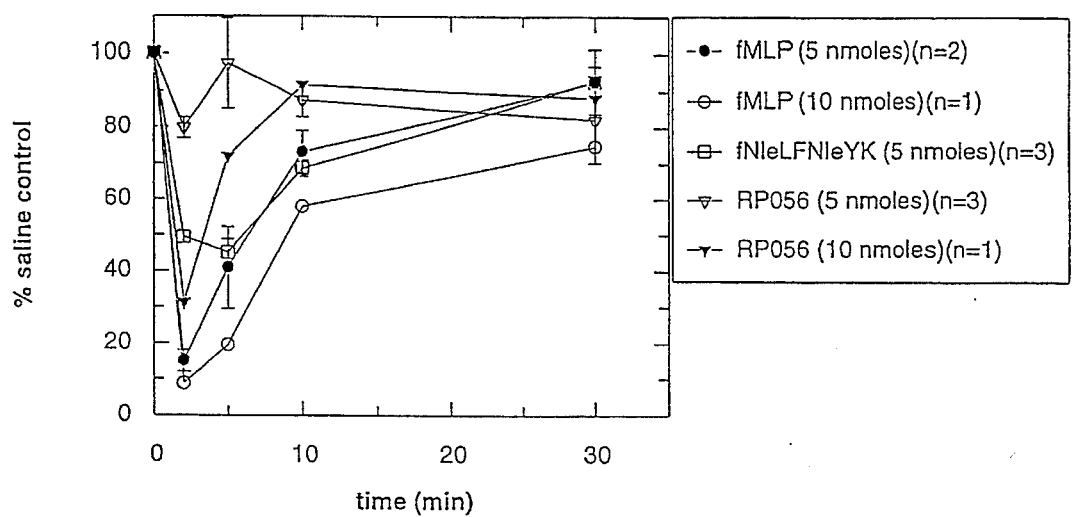
FIG. 2 is a graph representing neutropenic effect of targetting molecules in accordance with an embodiment of the invention.

Referring to FIG. 2, injections of 5 and 10 nmoles of fMLP produced a dose-dependent transient neutropenia, with a maximal effect occurring 2 min after peptide injection (15 and 9% of control respectively) returning to 93 and 75% of control values by 30 min after injection. 5 nmoles of formyl-Nleu-Leu-Phe-Nleu-Tyr-Lys produced a smaller maximal reduction in circulating neutrophils (45% of control) while RP-056 produced only a small transient drop in circulating neutrophils (80% of control) at 5 nmoles.

We claim:
1. A compound of the general formula:

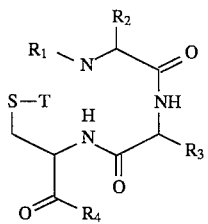

wherein
$R_1$ and $R_2$ together form a 5 - or 6 -membered heterocyclic ring which is optionally fused to a 5- or 6-membered ring, wherein either ring is optionally substituted with a conjugating group or with a conjugating group having a targetting molecule coupled thereto;

$R_3$ is selected from H; alkyl; and alkyl substituted by a group selected from amino, aminoacyl, carboxyl, guanidinyl, hydroxyl, thiol, phenyl, phenolyl, indolyl and imidazolyl;

$R_4$ is selected from hydroxyl; alkoxy; any amino acid residue; and a targetting molecule; and T is H or a sulfur protecting group;
with the proviso that $R_1$ and $R_2$ do not form a pyridine or pyrrolidine ring.

2. A compound according to claim 1, wherein the ring formed by $R_1$ and $R_2$ is a six membered heterocyclic ring.

3. A compound according to claim 1, wherein $R_1$ and $R_2$ together form a 6-carboxy substituted pyridine ring.

4. A compound according to claim 1, wherein $R_1$ and $R_2$ together form a 4-hydroxy- 6-carboxy substituted pyridine ring.

5. A compound according to claim 1 wherein $R_3$ is H.

6. A compound according to claim 1, wherein $R_3$ is the side chain of a serine amino acid residue.

7. A compound according to claim 1, wherein $R_1$ and $R_2$ together form a ring selected from a 6-carboxypyridine ring and a 6-carboxy-4-hydroxypyridine ring; $R_3$ is a serine amino acid side chain; T is Acm; and $R_4$ is -Gly-OH.

8. A compound according to claim 1, wherein $R_4$ is selected from -Gly-OH and -Gly-targetting molecule.

9. A compound according to claim 8, wherein the targetting molecule is a peptide.

10. A compound according to claim 9, wherein the peptide has a sequence selected from:

-NH-Lys-Pro-Pro-Arg-OH (SEQ. ID NO: 3)
-NH-Thr-Lys-Pro-Pro-Arg-OH (SEQ. ID NO: 2)

11. A compound according to claim 9, wherein the Gly forms an amide linkage with an ε-amino Lys residue of the peptide selected from:

-ε-amino Lys(-Gly-OH)-Tyr-Nleu-Phe-Leu-Nleu-formyl (SEQ. ID NO: 14)

-ε-amino Lys(-Asp-Gly-OH)-Lys-Tyr-Nleu-Phe-Leu-Nleu-formyl (SEQ. ID NO: 15).

12. A compound of the general formula:

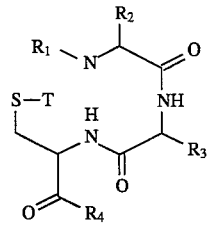

wherein $R_1$ and $R_2$ together form a pyridine ring; $R_3$ is H; T is Acm; and $R_4$ is -Gly-ε-amino Lys (-Gly-OH) -Tyr-Nleu-Phe-Leu-Nleu-formyl.

13. A compound of the general formula:

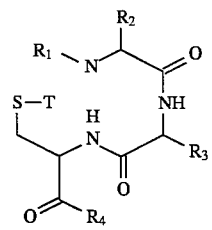

wherein $R_1$ and $R_2$ together form a pyridine ring; $R_3$ is a serine amino acid side chain; T is Acm; and $R_4$ is selected from:

-Gly-Lys-Pro-Pro-Arg-OH

-Gly-Thr-Lys-Pro-Pro-Arg-OH

-Gly-ε-amino Lys(-Gly-OH)-Tyr-Nleu-Phe-Leu-Nleu-formyl

-Gly-ε-amino Lys(-Asp-Gly-OH)-Lys-Tyr-Nleu-Phe-Leu-Nleuformyl-formyl.

14. A compound of the general formula:

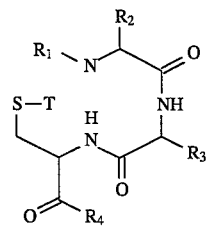

wherein:

$R_1$ and $R_2$ together form a 5- or 6-membered heterocyclic ring which is optionally fused to a 5- or 6-membered ring, wherein either ring is optionally substituted with a conjugating group or with a conjugating group having a targetting molecule coupled thereto or a hydroxyl group;

$R_3$ is selected from H; alkyl; and alkyl substituted by a group selected from amino, emlnoacyl, carboxyl, guanidinyl, hydroxyl, thiol, phenyl, phenolyl, indolyl end imidazolyl;

$R_4$ selected from hydroxyl; alkoxy; any areinc acid residue; and a targetting molecule; and T is H or a sulfur protecting group;

wherein the targetting molecule is a peptide having a sequence:

formyl-Nleu-Leu-Phe-Nleu-Tyr-Lys-Lys-Asp-X-OH (SEQ. ID NO: 1)

and X is a bond or any amino acid residue.

15. A compound according to claim 14, wherein X is -Gly-.

16. A compound having the formula:

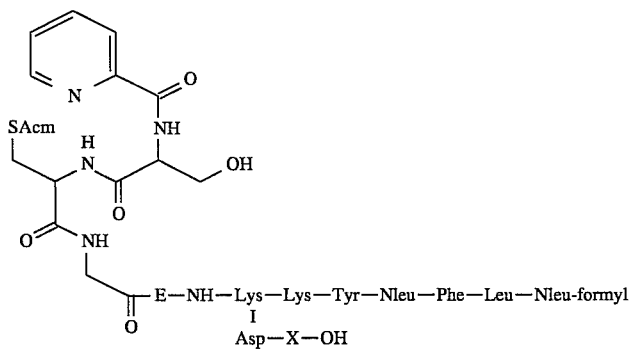

wherein X is a bond or -Gly-.

* * * * *